(12) United States Patent
Deckert et al.

(10) Patent No.: US 7,935,229 B2
(45) Date of Patent: May 3, 2011

(54) EXTRACTION OF NICKEL (0) COMPLEXES FROM NITRILE MIXTURES WITH REDUCED RAG FORMATION

(75) Inventors: Petra Deckert, Bammental (DE); Peter Bassler, Viernheim (DE); Michael Bartsch, Neustadt (DE); Gerd Haderlein, Grünstadt (DE); Hermann Luyken, Ludwigshafen (DE); Jens Scheidel, Hirschberg (DE); Peter Pfab, Neustadt (DE); Tobias Aechtner, Mannheim (DE); Wolfgang Siegel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 1054 days.

(21) Appl. No.: 11/577,231

(22) PCT Filed: Oct. 12, 2005

(86) PCT No.: PCT/EP2005/010956
§ 371 (c)(1),
(2), (4) Date: Apr. 13, 2007

(87) PCT Pub. No.: WO2006/042675
PCT Pub. Date: Apr. 27, 2006

(65) Prior Publication Data
US 2008/0083607 A1 Apr. 10, 2008

(30) Foreign Application Priority Data
Oct. 18, 2004 (DE) .......... 10 2004 050 935

(51) Int. Cl.
*B01D 3/34* (2006.01)
*B01D 11/04* (2006.01)
*B01J 31/40* (2006.01)
*B01J 38/56* (2006.01)
*C07C 253/32* (2006.01)

(52) U.S. Cl. ........ 203/43; 203/47; 203/59; 203/68; 203/94; 203/98; 502/24; 502/26; 502/31; 502/54; 558/335; 558/338

(58) Field of Classification Search ........ 203/2, 34, 203/38, 43–47, 51, 57, 59, 68–70, 94, 98; 502/24, 26, 31, 54; 558/335, 338
See application file for complete search history.

(56) References Cited

U.S. PATENT DOCUMENTS

| | | | |
|---|---|---|---|
| 3,773,809 A | 11/1973 | Walter | |
| 4,339,395 A | 7/1982 | Barnette et al. | |
| 4,385,007 A | 5/1983 | Shook, Jr. | |
| 4,990,645 A | 2/1991 | Back et al. | |
| 5,767,321 A * | 6/1998 | Billig et al. ............ | 568/454 |
| 5,847,191 A | 12/1998 | Bunel et al. | |
| 5,932,772 A | 8/1999 | Argyropoulos et al. | |
| 6,310,260 B1 * | 10/2001 | Argyropoulos et al. ...... | 568/454 |
| 2004/0140263 A1 | 7/2004 | Jackson et al. | |
| 2004/0204312 A1 * | 10/2004 | Jackson et al. ........... | 502/159 |
| 2006/0264651 A1 | 11/2006 | Bartsch et al. | |

FOREIGN PATENT DOCUMENTS

| | | |
|---|---|---|
| CA | 2553 778 | 8/2005 |
| CA | 2554 736 | 8/2005 |
| CA | 2553028 | 8/2005 |
| DE | 2154501 | 5/1972 |
| DE | 3235433 | 3/1983 |
| DE | 102004045036 | 3/2003 |
| DE | 10311122 | 9/2004 |
| DE | 10 2004004683 | 8/2005 |
| EP | 0464691 | 1/1992 |
| GB | 1361658 | 7/1974 |
| WO | WO-2004/062765 | 7/2004 |
| WO | WO-2005/073174 | 8/2005 |

* cited by examiner

*Primary Examiner* — Virginia Manoharan
(74) *Attorney, Agent, or Firm* — Connolly Bove Lodge & Hutz LLP

(57) ABSTRACT

A process for extractively removing homogeneously dissolved catalysts from a reaction effluent of a hydrocyanation of unsaturated mononitriles to dinitriles with a hydrocarbon H, including performing the steps of a) concentrating the reaction effluent before step b) by distillation at pressures of from 0.1 to 5000 mbar and temperatures of from 10 to 150° C., b) adding a hydrocarbon H to the concentrated reaction effluent to obtain a stream I, and c) feeding stream I, without prior separation of the liquid phases, into an extraction apparatus and extracting it at a temperature T with the hydrocarbon H to obtain a stream II comprising the hydrocarbon H enriched with the catalyst and a stream III having a low catalyst content.

17 Claims, No Drawings

EXTRACTION OF NICKEL (0) COMPLEXES FROM NITRILE MIXTURES WITH REDUCED RAG FORMATION

This application is the National Phase of International Application No. PCT/EP2005/010956 filed on Oct. 12, 2005; and this application claims priority to Application No. 102004050935.2 filed in Germany on Oct. 18, 2004 under 35 U.S.C. §119; the entire contents of all are hereby incorporated by reference.

The invention relates to a process for extractively removing homogeneously dissolved catalysts from a reaction effluent of a hydrocyanation of unsaturated mononitriles to dinitriles, by extraction by means of a hydrocarbon H, which comprises
a) adding a nonpolar aprotic liquid L to the reaction effluent to obtain a stream I, and
b) extracting the stream I at a temperature T with the hydrocarbon H to obtain a stream II comprising the hydrocarbon H enriched with the catalyst and a stream III having a low catalyst content.

For hydrocyanations of unsaturated mononitriles, nickel complexes of phosphorus ligands, for example, are suitable catalysts. For example, adiponitrile, an important intermediate in polyamide production, is prepared by double hydrocyanation of 1,3-butadiene. In a first hydrocyanation, 1,3-butadiene is reacted with hydrogen cyanide in the presence of nickel(0) which is stabilized with phosphorus ligands to give 3-pentenenitrile. In a second hydrocyanation, 3-pentenenitrile is subsequently reacted with hydrogen cyanide to give adiponitrile, likewise over a nickel(0) catalyst, but if appropriate with addition of a promoter, for example of a Lewis acid. Nickel(0) or Ni(0) means nickel in the zero oxidation state.

In order to increase the economic viability of the hydrocyanation, the nickel catalyst is typically removed and recycled (catalyst circulation). Since the catalyst system in the second hydrocyanation, which is a mixture of complex and free ligand, cannot be thermally stressed to a high degree, the high-boiling adiponitrile cannot be removed from the catalyst system by distillation. Therefore, the separation is generally carried out extractively using cyclohexane or methylcyclohexane or other hydrocarbons as the extractant. The catalyst system remains ideally fully, under real conditions at least partly, in the lighter hydrocarbon phase, while the heavier phase is more polar and comprises crude adiponitrile and, where present, the Lewis acid. After the phase separation, the extractant is removed generally by distillation under reduced pressure. The boiling pressure of the extractant is distinctly higher than that of the adiponitrile.

In the course of the extraction, undesired rag formation can occur. Rag refers to a region of incomplete phase separation between upper and lower phase, usually a liquid/liquid mixture in which solids may also be dispersed. Excess rag formation is undesired since it hinders the extraction and the extraction apparatus can under some circumstances be flooded by rag, as a result of which it can no longer fulfill its separation task.

U.S. Pat. Nos. 3,773,809 and 5,932,772 describe the extraction of the catalyst complex and of the ligands with paraffins and cycloparaffins, for example cyclohexane, heptane and octane, or alkylaromatics.

U.S. Pat. No. 4,339,395 discloses a process for extractively working up reaction effluents of hydrocyanations for catalyst systems having monodentate ligands and a triarylborane as a promoter, in which a small amount of ammonia is metered in in order to prevent rag formation.

WO 2004/062765 describes the extractive removal of a nickel diphosphite catalyst from a mixture of mono- and dinitriles with alkanes or cycloalkanes as an extractant, wherein the mixture is treated with a Lewis base, for example organoamines or ammonia.

U.S. Pat. No. 5,847,191 discloses a process for the extractive workup of reaction effluents of hydrocyanations, wherein the chelate ligands bear $C_9$- to $C_{40}$-alkyl radicals.

U.S. Pat. No. 4,990,645 states that the extractability of the nickel complex and of the free ligand can be improved when the $Ni(CN)_2$ solid formed in the reaction is removed in a decanter before the extraction. To this end, a portion of the pentene nitrile is evaporated off beforehand in order to reduce the solubility of the catalyst and of the $Ni(CN)_2$.

The prior German patent application DE 102004 045036.6 of Sep. 15, 2004, which had not been published at the priority date of the present application, describes the extraction of Ni(0) complexes having phosphorus ligands and/or free phosphorus ligands from the effluent of a hydrocyanation reaction by means of a hydrocarbon under particular boundary conditions. A treatment of the effluent with nonpolar aprotic liquids before the extraction is not mentioned.

It is an object of the present invention to remedy the disadvantages outlined. The intention is to provide a process for extractively removing homogeneously dissolved catalysts, for example nickel(0) complexes having phosphorus ligands and/or free phosphorus ligands, from a reaction effluent of a hydrocyanation of unsaturated mononitriles to dinitriles, which avoids the above-described disadvantages of the known processes. In particular, the process should distinctly reduce or completely prevent the formation of rag, and thus enable undisrupted operation of the extraction apparatus.

At the same time, the efficiency of the extraction, in particular the recovery of the catalyst in the hydrocarbon phase, should not be reduced.

Accordingly, the process mentioned at the outset has been found. Preferred embodiments of the invention can be taken from the subclaims.

The catalyst is dissolved homogeneously in the reaction effluent. In principle, useful catalysts are all compounds which catalyze the hydrocyanation of mononitriles to dinitriles. The catalyst is preferably a nickel(0) complex having phosphorus ligands and/or free phosphorus ligands. These Ni(0) complexes and ligands, and also Lewis acids and promoters used if appropriate, are described below; first, the process according to the invention is illustrated.

In a particularly preferred embodiment, the process according to the invention is used in the preparation of adiponitrile. Thus, the process according to the invention is intended preferentially for 3-pentenenitrile as the mononitrile and adiponitrile as the dinitrile. Preference is equally given to obtaining the reaction effluent of the hydrocyanation by reacting 3-pentenenitrile with hydrogen cyanide in the presence of at least one nickel(0) complex having phosphorus ligands, if appropriate in the presence of a promoter, for example at least one Lewis acid.

The process according to the invention is suitable for extractively removing homogeneously dissolved catalysts, in particular Ni(0) complexes, which contain phosphorus ligands and/or free phosphorus ligands, from a reaction effluent which is obtained in the hydrocyanation of unsaturated mononitriles to dinitriles.

If necessary, the reaction effluent may be concentrated, for example to from 5 to 70%, preferably from 15 to 60%, of its original volume before step a) by distillation, for example at pressures of from 0.1 to 5000 mbar (abs.), preferably from 0.5 to 1000 mbar (abs.) and in particular from 1 to 200 mbar (abs.), and temperatures of from 10 to 150° C., preferably from 40 to 100° C., or other suitable measures.

Step a): Addition of the Nonpolar Aprotic Liquid L

In step a), a nonpolar aprotic liquid L is added to the reaction effluent to obtain a stream I. In this context, liquid means that the compound L is present in liquid form at least under the pressure and temperature conditions in step a); under other pressure and temperature conditions, L may also be solid or gaseous.

Suitable nonpolar aprotic liquids L are all compounds which are liquid under the conditions of step a) and which do not significantly chemically or physically alter the catalyst, for example the Ni(0) complex having phosphorus ligands and/or the free phosphorus ligands, if at all. Compounds suitable as the liquid L do not contain an ionizable proton in the molecule and generally have low relative dielectric constants ($\epsilon_r$<15) and low electrical dipole moments ($\mu$<2.5 Debye).

Especially suitable are hydrocarbons which may, for example, be unhalogenated or halogenated, and also amines, especially tertiary amines, and carbon disulfide.

In a preferred embodiment, the liquid L is a hydrocarbon H*. Suitable hydrocarbons H* are aliphatic, cycloaliphatic or aromatic. Suitable aliphatic hydrocarbons are, for example, linear or branched alkanes or alkenes having from 5 to 30, preferably from 5 to 16, carbon atoms, in particular pentane, hexane, heptane, octane, nonane, decane, undecane and dodecane (in each case all isomers).

Suitable cycloaliphatic hydrocarbons have, for example, from 5 to 10 carbon atoms, such as cyclopentane, cyclohexane, cycloheptane, cyclooctane, cyclononane and cyclodecane. Substituted, in particular $C_{1-10}$-alkyl-substituted, cycloaliphatics such as methylcyclohexane are also suitable. Suitable aromatic hydrocarbons are preferably those having from 6 to 20 carbon atoms, in particular benzene, toluene, o-, m- and p-xylene, naphthalene and anthracene. It is also possible to use substituted, preferably $C_{1-10}$-alkyl-substituted, aromatics such as ethylbenzene.

The hydrocarbon H* is more preferably selected from the compounds mentioned below for the hydrocarbon H. Very particular preference is given to the hydrocarbon H* being identical to the hydrocarbon H, i.e. the same hydrocarbon is used for the extraction and as the liquid L.

Configuration of the Addition of the Liquid

The nonpolar aprotic liquid may be added to the reaction effluent in customary mixer apparatus. Because it is particularly simple from a process technology point of view, preference is given to mixing the nonpolar aprotic liquid L with the reaction effluent in step a) in a stirred vessel or a pumped circulation system.

Preference is given to mixing the nonpolar aprotic liquid intimately with the reaction effluent. Suitable stirred vessels are customary liquid mixers which may be provided with intensively mixing mixer elements and/or static or mobile internals.

Preference is likewise given to the use of a pumped circulation system. It is typically operated in such a way that the ratio of amount pumped in circulation to expulsion from the pumped circuit is from 0.1:1 to 1000:1, preferably from 1:1 to 100:1 and more preferably from 2:1 to 25:1. Suitable circulation pumps are, for example, gear pumps or other customary pumps. The circulation pump preferably works against an overflow valve which opens at a defined pressure of, for example, from 3 to 10 bar (abs.).

When the same hydrocarbon is used in step a) and b), it is possible in both steps to use fresh hydrocarbon in each case. It is equally possible to re-use the hydrocarbon used in step a) in step b), or to recycle the hydrocarbon used in step b) to step a) and reuse it there.

In a very particularly preferred embodiment, the liquid L is part of stream II (catalyst-enriched hydrocarbon H, see below) which is obtained in step b). This means that a portion of stream II is branched off in step b) and the branched-off portion is added to the reaction effluent in step a). In this embodiment, a portion of stream II is accordingly circulated.

In another, likewise preferred embodiment, the nonpolar aprotic liquid L is metered directly into a delay zone (see below), for example at the start thereof.

The liquid L is added generally at temperatures of from 0 to 150° C., preferably from 10 to 100° C. and in particular from 20 to 80° C., and pressures of from 0.01 to 100 bar (abs.), preferably from 0.1 to 10 bar (abs.) and in particular from 0.5 to 5 bar (abs.).

The required amount of the liquid L may vary within wide limits. It is generally lower than the amount of the hydrocarbon H used, with which extraction is effected in step b), but may also be larger. The amount of the liquid L is preferably from 0.1 to 200% by volume, in particular from 1 to 50% by volume and more preferably from 5 to 30% by volume, based on the amount of the hydrocarbon H used for the extraction in step b).

Particular preference is given to adding the liquid L in an amount which is sufficient in order to achieve a phase separation in stream I before it is fed into the extraction (step b)). In this embodiment, the biphasic stream I is conducted through a delay zone (on this subject, see below) after step a) and before step b). The delay zone functions as a decanter and separates the two phases of stream I from one another. The removed first phase comprises the predominant portion of the ingredients of the reaction effluent which has been concentrated if appropriate, and fractions of the catalyst to be extracted, and is fed into the extraction apparatus. The removed second phase which is obtained in addition to the first phase is likewise fed into the extraction apparatus, usually at another point, together with the hydrocarbon H (extractant). Preference is given to bringing about countercurrent flow of the phases. In this embodiment, stream I is accordingly fed to the extraction as two separate phases.

In another, likewise particularly preferred embodiment, the biphasic stream I is conducted into the extraction apparatus without separation of the phases, i.e. both phases together at the same place and time. This is preferably effected in countercurrent to the hydrocarbon H (extractant).

Optional Treatment with Ammonia or Amine

In a preferred embodiment of the process according to the invention, the reaction effluent of the hydrocyanation is treated before step a), or stream I is treated during or after step a) or during step b), with ammonia or a primary, secondary or tertiary, aromatic or aliphatic amine. Aromatic includes alkylaromatic, and aliphatic includes cycloaliphatic.

It has been found that this ammonia or amine treatment can reduce the content of catalyst, in particular of nickel(0) complex or ligand, in the second phase enriched with dinitriles (stream III) in the course of the extraction (step b)), i.e. the distribution of Ni(0) complex or of the ligands between the two phases is shifted in favor of the first phase (stream II) in the course of the extraction. The ammonia or amine treatment improves the catalyst enrichment in stream II; this means lower catalyst losses in the catalyst cycle and increases the economic viability of the hydrocyanation.

Accordingly, in this embodiment, the extraction is preceded by a treatment of the reaction effluent, or of stream I, with ammonia or an amine, or this is effected during the extraction. The treatment during the extraction is less preferred.

Particular preference is given to adding the ammonia or the amine together with the nonpolar aprotic liquid L. In particular, the liquid L and the ammonia or amine are added in the same mixing apparatus.

The amines used are monoamines, diamines, triamines or more highly functional amines (polyamines). The monoamines typically have alkyl radicals, aryl radicals or arylalkyl radicals having from 1 to 30 carbon atoms; suitable monoamines are, for example, primary amines, e.g. monoalkylamines, secondary or tertiary amines, e.g. dialkylamines. Suitable primary monoamines are, for example, butylamine, cyclohexylamine, 2-methylcyclohexylamine, 3-methylcyclohexylamine, 4-methylcyclohexylamine, benzylamine, tetrahydrofurfurylamine and furfurylamine. Useful secondary monoamines are, for example, diethylamine, dibutylamine, di-n-propylamine and N-methylbenzylamine. Suitable tertiary amines are, for example, trialkylamines having $C_{1-10}$-alkyl radicals such as trimethylamine, triethylamine or tributylamine.

Suitable diamines are, for example, those of the formula $R^1$—NH—$R^2$—NH—$R^3$, where $R^1$, $R^2$ and $R^3$ are each independently hydrogen or an alkyl radical, aryl radical or arylalkyl radical having from 1 to 20 carbon atoms. The alkyl radical may be linear or, especially for $R^2$, also cyclic. Suitable diamines are, for example, ethylenediamine, propylenediamines (1,2-diaminopropane and 1,3-diaminopropane), N-methyl-ethylenediamine, piperazine, tetramethylenediamine (1,4-diaminobutane), N,N'-dimethylethylenediamine, N-ethylethylenediamine, 1,5-diaminopentane, 1,3-diamino-2,2-diethylpropane, 1,3-bis(methylamino)propane, hexamethylenediamine (1,6-diaminohexane), 1,5-diamino-2-methylpentane, 3-(propylamino)propylamine, N,N'-bis(3-aminopropyl)piperazine, N,N'-bis(3-aminopropyl) piperazine and isophoronediamine (IPDA).

Suitable triamines, tetramines or more highly functional amines are, for example, tris(2-aminoethyl)amine, tris(2-aminopropyl)amine, diethylenetriamine (DETA), triethylenetetramine (TETA), tetraethylenepentamine (TEPA), isopropylenetriamine, dipropylenetriamine and N,N'-bis(3-aminopropylethylenediamine). Aminobenzylamines and aminohydrazides having 2 or more amino groups are likewise suitable.

Of course, it is also possible to use mixtures of ammonia with one or more amines, or mixtures of a plurality of amines.

Preference is given to using ammonia or aliphatic amines, in particular trialkylamines having from 1 to 10 carbon atoms in the alkyl radical, for example trimethylamine, triethylamine or tributylamine, and also diamines such as ethylenediamine, hexamethylenediamine or 1,5-diamino-2-methylpentane.

Particular preference is given to ammonia alone; in other words, particular preference is given to using no amine apart from ammonia. Very particular preference is given to anhydrous ammonia; in this case, anhydrous means a water content below 1% by weight, preferably below 1000 ppm by weight and in particular below 100 ppm by weight.

The molar ratio of amine to ammonia may be varied within wide limits, and is generally from 10 000:1 to 1:10 000.

The amount of the ammonia or amine used depends, inter alia, on the type and amount of the catalyst, for example of the nickel(0) catalyst and/or of the ligands, and, if used, on the type and amount of the Lewis acid which is used as a promoter in the hydrocyanation. Typically, the molar ratio of ammonia or amine to Lewis acid is at least 1:1. The upper limit of this molar ratio is generally uncritical and is, for example, 100:1; however, the excess of ammonia or amine should not be so great that the Ni(0) complex or its ligand decomposes. The molar ratio of ammonia or amine to Lewis acid is preferably from 1:1 to 10:1, more preferably from 1.5:1 to 5:1, and in particular about 2.0:1. When a mixture of ammonia and amine is used, these molar ratios apply to the sum of ammonia and amine.

The temperature in the treatment with ammonia or amine is typically not critical and is, for example, from 10 to 140° C., preferably from 20 to 100° C. and in particular from 20 to 90° C. The pressure is generally not critical either.

The ammonia or the amine may be added to the reaction effluent in gaseous form, in liquid form (under pressure) or dissolved in a solvent. Suitable solvents are, for example, nitrites, especially those which are present in the hydrocyanation, and also aliphatic, cycloaliphatic or aromatic hydrocarbons, as used in the process according to the invention as extractants, for example cyclohexane, methylcyclohexane, n-heptane or n-octane.

The ammonia or amine addition is effected in customary apparatus, for example those for gas introduction or in liquid mixers. The solid which precipitates out in many cases may either remain in the reaction effluent, i.e. a suspension is fed to the extraction, or be removed as described below.

Optional Removal of the Solids

In a preferred embodiment, solids which precipitate out in step a) of the process are removed from stream I before the extraction (step b)).

In many cases, this allows the extraction performance of the process according to the invention to be improved further, since solids which occur often reduce the separating performance of the extraction apparatus. It has also been found that a removal of solids before the extraction often distinctly reduces or fully suppresses the undesired rag formation.

Preference is given to configuring the solids removal in such a way that the solid particles having a hydraulic diameter of greater than 5 μm, in particular greater than 1 μm and more preferably greater than 100 nm are removed.

For the solids removal, it is possible to use customary processes, for example filtration, crossflow filtration, centrifugation, sedimentation, classification or preferably decantation, for which common apparatus such as filters, centrifuges and decanters can be used.

Temperature and pressure in the solids removal are typically not critical. For example, it is possible to work within the temperature and pressure ranges specified above or below.

The solids removal may be effected before, during or after the optional treatment of the reaction effluent, or of stream I, with ammonia or amine. The removal is preferably during or after the ammonia or amine treatment, more preferably thereafter.

When the solids are removed during or after the amine or ammonia treatment, the solids are usually compounds of ammonia or amine with the Lewis acid used or the promoter which are sparingly soluble in the reaction effluent. When, for example, $ZnCl_2$ is used, substantially sparingly soluble $ZnCl_2.2NH_3$ precipitates out in the course of the ammonia treatment.

When the solids are removed before the ammonia or amine treatment, or if there is no treatment with ammonia or amine at all, the solids are generally nickel compounds of the +II oxidation state, for example nickel(II) cyanide or similar cyanide-containing nickel(II) compounds, or Lewis acids or compounds thereof. The compounds mentioned may precipitate out, for example, because their solubility has been reduced by temperature change, for example.

Optional Delay Zone

Stream I as the effluent from step a) may be transferred directly into step b), for example through a pipeline. In this context, directly means that the average residence time of stream I in the pipeline is less than 1 min.

However, in a preferred embodiment of the process according to the invention, stream I is conducted through a delay zone after step a) and before step b). Consequently, the delay zone is disposed downstream of the addition of the liquid L and upstream of the extraction.

Suitable delay zones are, for example, pipelines, static mixers, stirred or unstirred vessels or vessel batteries, and also combinations of these elements. The delay zone is preferably configured and designed in such a way that the average residence time of stream I in the delay zone is at least 1 min, preferably at least 5 min.

The optional solids removal described above may also be effected in the delay zone. In this case, the delay zone serves as a calming zone in which the solid can sediment. In this way, the delay zone functions as a decanter or crossflow filter. It may be provided with devices for conveying and/or for discharging solids.

As is mentioned, in a preferred embodiment, the nonpolar aprotic liquid L is metered directly into the delay zone, for example at the start thereof. In this embodiment, particular preference is given to selecting a delay zone which ensures intimate mixing of reaction effluent and liquid L. As likewise already described, the delay zone may bring about a phase separation of the stream I.

The delay zone is generally operated at temperatures of from 0 to 200° C., preferably from 10 to 150° C. and in particular from 20 to 100° C., and pressures of from 0.01 to 100 bar (abs.), preferably from 0.1 to 10 bar (abs.) and in particular from 0.5 to 5 bar (abs.).

In a preferred embodiment of the invention, the flow rate of stream I in all pipelines used in the process according to the invention is at least 0.5 m/s, in particular at least 1 m/s and more preferably at least 2 m/s.

The stream I obtained in step a), if appropriate after the treatment with ammonia or amines, and/or after the solids removal, and/or after passing through the delay zone, is extracted in step b).

Step b): Extraction of Stream I with the Hydrocarbon H

In step b), the stream I obtained in step a) is extracted with a hydrocarbon H at a temperature T; this gives a stream II comprising the hydrocarbon H enriched with the catalyst and a stream III having a low catalyst content. A first phase (stream II) which is enriched in catalyst compared to the reaction effluent and a second phase (stream III) which is enriched in dinitriles compared to the reaction effluent form. Usually, stream II is the lighter phase, i.e. the upper phase, and stream III the heavier phase, i.e. the lower phase.

Depending on the phase ratio, the extraction has an extraction coefficient, defined as the ratio of the mass content of catalyst, for example the nickel(0) complexes and ligands mentioned, in stream II to the mass content of catalyst in stream III, for each theoretical extraction stage of preferably from 0.1 to 10, more preferably from 0.8 to 5. The extractive action, measured by the extraction coefficient, for the free ligand is equally good or better, preferably better, than for the nickel(0) complex.

After the phase separation, stream II contains preferably between 50 and 99% by weight, more preferably between 60 and 97% by weight, in particular between 80 and 95% by weight, of the hydrocarbon used for the extraction without taking into account the nonpolar aprotic liquid L added.

The Lewis acid which is, if appropriate (specifically in the second hydrocyanation mentioned at the outset), present in the feedstream of the extraction (stream I) remains preferably for the most part and more preferably fully in the lower phase (stream III). Here, fully means that the residual concentration of the Lewis acid in the upper phase (stream II) is preferably less than 1% by weight, more preferably less than 0.5% by weight, in particular less than 500 ppm by weight.

Hydrocarbon H

The hydrocarbon is the extractant. It has a boiling point of preferably at least 30° C., more preferably at least 60° C., in particular at least 90° C., and preferably at most 140° C., more preferably at most 135° C., in particular at most 130° C., in each case at a pressure of $10^5$ Pa absolute.

Particular preference is given to using a hydrocarbon, this referring in the context of the present invention either to an individual hydrocarbon or to a mixture of such hydrocarbons, for the removal, especially by extraction, of adiponitrile from a mixture comprising adiponitrile and the catalyst (for example containing Ni(0)), said hydrocarbon having a boiling point in the range between 90° C. and 140° C. The catalyst, if appropriate with addition of a suitable solvent which is higher-boiling than the hydrocarbon H (e.g. pentenenitrile), may advantageously be obtained from the mixture obtained after the removal according to this process by distillatively removing the hydrocarbon. The use of a hydrocarbon having a boiling point in the range specified permits a particularly economically viable and technically simple removal, since the hydrocarbon which has been distilled off can be condensed with river water.

Suitable hydrocarbons are described, for example, in U.S. Pat. No. 3,773,809, column 3, lines 50-62. Preference is given to a hydrocarbon selected from cyclohexane, methylcyclohexane, cycloheptane, n-hexane, n-heptane, isomeric heptanes, n-octane, isooctane, isomeric octanes such as 2,2,4-trimethylpentane, cis- and trans-decalin or mixtures thereof, especially of cyclohexane, methylcyclohexane, n-heptane, isomeric heptanes, n-octane, isomeric octanes such as 2,2,4-trimethylpentane, or mixtures thereof. Particular preference is given to using cyclohexane, methylcyclohexane, n-heptane or n-octane.

Very particular preference is given to n-heptane or n-octane. With these hydrocarbons, the undesired rag formation is particularly low.

The hydrocarbon used is preferably anhydrous, anhydrous meaning a water content of below 100 ppm by weight, preferably below 50 ppm by weight, in particular below 10 ppm by weight. The hydrocarbon may be dried by suitable processes known to those skilled in the art, for example by adsorption or azeotropic distillation. The drying may be effected in a step preceding the process according to the invention.

As is mentioned, in a preferred embodiment, the hydrocarbon H is also used as the nonpolar aprotic liquid L.

Configuration of the Extraction

The extraction of the catalyst, for example of the nickel(0) complexes or ligands, from stream I may be carried out in any suitable apparatus known to those skilled in the art, preferably in countercurrent extraction columns, mixer-settler units or combinations of mixer-settler units with columns. Particular preference is given to the use of countercurrent extraction columns which are equipped in particular with sheet metal packings as dispersing elements. In a further particularly preferred embodiment, the extraction is performed in countercurrent in a compartmented, stirred extraction column.

Regarding the dispersion direction, in a preferred embodiment of the process, the hydrocarbon H is used as the continuous phase and stream I as the disperse phase. This generally also shortens the phase separation time and reduces rag formation. However, the reverse dispersion direction is also possible, i.e. stream I as the continuous phase and hydrocarbon as the disperse phase, especially when the rag formation can be suppressed fully. Typically, the dispersion direction more favorable for the separating performance of the extraction apparatus is selected.

In the extraction, a phase ratio of preferably from 0.1 to 10, more preferably from 0.4 to 2.5, in particular from 0.75 to 1.5, calculated in each case as the ratio of mass of the hydrocarbon H added to mass of stream I, is used.

The absolute pressure during the extraction is preferably from 10 kPa to 1 MPa, more preferably from 50 kPa to 0.5 MPa, in particular from 75 kPa to 0.25 MPa (absolute).

The extraction is preferably carried out at a temperature T of from −15 to 120° C., in particular from 20 to 100° C. and more preferably from 30 to 80° C. It has been found that the rag formation is lower at a higher temperature of the extraction.

In a particularly preferred embodiment, the extraction is operated with a temperature profile. In particular, operation is effected in this case at an extraction temperature of at least 60° C., preferably from 60 to 95° C. and more preferably at least 70° C.

The temperature profile is preferably configured in such a way that, in that region of the extraction in which the content of catalyst, for example of nickel(0) complexes having phosphorus ligands and/or free phosphorus ligands is higher than in the other region, the temperature is lower than in the other region. In this way, the thermally labile Ni(0) complexes are less thermally stressed and their decomposition is reduced.

Where an extraction column, for example, is used for the extraction and a temperature profile is employed, the lowest temperature is established at the top of the column and the highest at the bottom of the column. The temperature differential between top and bottom of the column may be, for example, from 0 to 30° C., preferably from 10 to 30° C. and in particular from 20 to 30° C.

In a particularly preferred embodiment, stream I is adjusted before the extraction to a temperature T* which is at least 5° C., in particular at least 10° C. and more preferably at least 20° C., below the temperature T at which the extraction is effected. Instead of stream I, it is also possible to adjust the reaction effluent even before step a), or the nonpolar aprotic liquid L to be added, to the temperature T* specified. The advantageous cooling of stream I may thus also be effected by not actually cooling stream I, but rather one or both of its constituents (reaction effluent or liquid L) beforehand.

Accordingly, in the process, at least one of the three streams, reaction effluent, nonpolar aprotic liquid L and stream I, is preferably adjusted to a temperature T* which is at least 5° C., in particular at least 10° C. and more preferably at least 20° C., below the temperature T. Particular preference is given to a temperature differential ΔT=T−T* at which sedimentation of solids in the extraction stage b) is prevented.

In some cases, it may be advantageous, after the cooling to the lower temperature T*, to heat the reaction effluent, the liquid L or the stream I again before entry into the extraction, for example to the temperature T.

Configuration of the Phase Separation

Depending on the apparatus configuration, in terms of space and time, the phase separation may also be viewed as the last part of the extraction. For the phase separation, a wide pressure, concentration and temperature range may typically be selected, and the optimal parameters for the particular composition of the reaction mixture can be determined readily by a few simple preliminary experiments.

The temperature in the phase separation is typically at least 0° C., preferably at least 10° C., more preferably at least 20° C. Typically, it is at most 120° C., preferably at most 100° C., more preferably at most 95° C. For example, the phase separation is carried out at from 0 to 100° C., preferably from 60 to 95° C. It has been found that the rag formation is lower at a higher temperature of the phase separation.

The pressure in the phase separation is generally at least 1 kPa, preferably at least 10 kPa, more preferably 20 kPa. In general, it is at most 2 MPa, preferably at most 1 MPa, more preferably at most 0.5 MPa absolute.

The phase separation time, i.e. the duration from the mixing of stream I with the hydrocarbon H (extractant) to the formation of a uniform upper phase and a uniform lower phase may vary within wide limits. The phase separation time is generally from 0.1 to 60 min, preferably from 1 to 30 min and in particular from 2 to 10 min. When the process according to the invention is carried out on the industrial scale, a maximum phase separation time of 15 min, in particular 10 min, is typically technically and economically sensible.

It has been found that the phase separation time is reduced in an advantageous manner especially when long-chain aliphatic alkanes such as n-heptane or n-octane are used as the hydrocarbon H.

The phase separation may be carried out in one or more apparatuses, known to those skilled in the art for such phase separations. In an advantageous embodiment, the phase separation may be carried out in the extraction apparatus, for example in one or more mixer-settler combinations or by equipping an extraction column with a calming zone.

In the phase separation, two liquid phases are obtained, of which one phase (stream II) has a higher proportion of catalyst, for example the nickel(0) complex having phosphorus ligands and/or free phosphorus ligands, based on the total weight of this phase, than the other phase (stream III).

Nickel(0) Complexes and Ligands

The nickel(0) complexes which are used with preference as catalyst and contain phosphorus ligands and/or free phosphorus ligands are preferably homogeneously dissolved nickel (0) complexes.

The phosphorus ligands of the nickel(0) complexes and the free phosphorus ligands, which are removed by extraction in accordance with the invention, are preferably selected from mono- or bidentate phosphines, phosphites, phosphinites and phosphonites.

These phosphorus ligands preferably have the formula I $$P(X^1R^1)(X^2R^2)(X^3R^3) \qquad (I).$$

In the context of the present invention, compound I is a single compound or a mixture of different compounds of the aforementioned formula.

According to the invention, $X^1$, $X^2$, $X^3$ each independently are oxygen or a single bond. When all of the $X^1$, $X^2$ and $X^3$ groups are single bonds, compound I is a phosphine of the formula $P(R^1R^2R^3)$ with the definitions of $R^1$, $R^2$ and $R^3$ specified in this description.

When two of the $X^1$, $X^2$ and $X^3$ groups are single bonds and one is oxygen, compound I is a phosphinite of the formula $P(OR^1)(R^2)(R^3)$ or $P(R^1)(OR^2)(R^3)$ or $P(R^1)(R^2)(OR^3)$ with the definitions of $R^1$, $R^2$ and $R^3$ specified below.

When one of the $X^1$, $X^2$ and $X^3$ groups is a single bond and two are oxygen, compound I is a phosphonite of the formula $P(OR^1)(OR^2)(R^3)$ or $P(R^1)(OR^2)(OR^3)$ or $P(OR^1)(R^2)(OR^3)$ with the definitions of $R^1$, $R^2$ and $R^3$ specified in this description.

In a preferred embodiment, all $X^1$, $X^2$ and $X^3$ groups should be oxygen, so that compound I is advantageously a phosphite of the formula $P(OR^1)(OR^2)(OR^3)$ with the definitions of $R^1$, $R^2$ and $R^3$ specified below.

According to the invention, $R^1$, $R^2$, $R^3$ are each independently identical or different organic radicals. $R^1$, $R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference is given to the $R^1$, $R^2$ and $R^3$ groups not being bonded together directly.

In a preferred embodiment, $R^1$, $R^2$ and $R^3$ groups are radicals selected from the group consisting of phenyl, o-tolyl, m-tolyl and p-tolyl. In a particularly preferred embodiment, a maximum of two of the $R^1$, $R^2$ and $R^3$ groups should be phenyl groups.

In another preferred embodiment, a maximum of two of the $R^1$, $R^2$ and $R^3$ groups should be o-tolyl groups.

Particularly preferred compounds I which may be used are those of the formula Ia

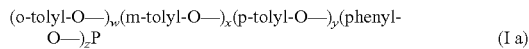

where w, x, y, and z are each a natural number where $w+x+y+z=3$ and $w, z \leq 2$.

Such compounds 1a are, for example, (p-tolyl-O—)(phenyl-O—)$_2$P, (m-tolyl-O—)(phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O—)(phenyl-O—)P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P, (o-tolyl-O—)$_2$(m-tolyl-O—)P or mixtures of such compounds.

For example, mixtures comprising (m-tolyl-O—)$_3$P, (m-tolyl-O—)$_2$(p-tolyl-O—)P, (m-tolyl-O—)(p-tolyl-O—)$_2$P and (p-tolyl-O—)$_3$P may be obtained by reacting a mixture comprising m-cresol and p-cresol, in particular in a molar ratio of 2:1, as obtained in the distillative workup of crude oil, with a phosphorus trihalide, such as phosphorus trichloride.

In another, likewise preferred embodiment, the phosphorus ligands are the phosphites, described in detail in DE-A 199 53 058, of the formula I b:

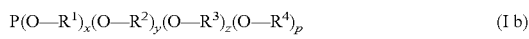

where $R^1$: aromatic radical having a $C_1$-$C_{18}$-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, $R^2$: aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, $R^3$: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, $R^4$: aromatic radical which bears substituents other than those defined for $R^1$, $R^2$ and $R^3$ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y, z, p: each independently 0, 1 or 2, with the proviso that $x+y+z+p=3$.

Preferred phosphites of the formula I b can be taken from DE-A 199 53 058. The $R^1$ radical may advantageously be o-tolyl, o-ethylphenyl, o-n-propylphenyl, o-isopropylphenyl, o-n-butylphenyl, o-sec-butylphenyl, o-tert-butylphenyl, (o-phenyl)phenyl or 1-naphthyl groups.

Preferred $R^2$ radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous $R^3$ radicals are p-tolyl, p-ethylphenyl, p-n-propylphenyl, p-isopropylphenyl, p-n-butylphenyl, p-sec-butylphenyl, p-tert-butylphenyl or (p-phenyl)phenyl groups.

The $R^4$ radical is preferably phenyl. p is preferably zero. For the indices x, y, z and p in compound I b, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula I b are those in which p is zero, and $R^1$, $R^2$ and $R^3$ are each independently selected from o-isopropylphenyl, m-tolyl and p-tolyl, and $R^4$ is phenyl.

Particularly preferred phosphites of the formula I b are those in which $R^1$ is the o-isopropylphenyl radical, $R^2$ is the m-tolyl radical and $R^3$ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical, $R^2$ is the 2-naphthyl radical and $R^3$ is the p-tolyl radical with the indices specified in the table; and finally those in which $R^1$ is the o-isopropylphenyl radical, $R^2$ is the 2-naphthyl radical and $R^3$ is the p-tolyl radical with the indices specified in the table; and also mixtures of these phosphites.

Phosphites of the formula I b may be obtained by
a) reacting a phosphorus trihalide with an alcohol selected from the group consisting of $R^1OH$, $R^2OH$, $R^3OH$ and $R^4OH$ or mixtures thereof to obtain a dihalophosphorous monoester,
b) reacting the dihalophosphorous monoester mentioned with an alcohol selected from the group consisting of $R^1OH$, $R^2OH$, $R^3OH$ and $R^4OH$ or mixtures thereof to obtain a monohalophosphorous diester and
c) reacting the monohalophosphorous diester mentioned with an alcohol selected from the group consisting of $R^1OH$, $R^2OH$, $R^3OH$ and $R^4OH$ or mixtures thereof to obtain a phosphite of the formula I b.

The reaction may be carried out in three separate steps. Equally, two of the three steps may be combined, i.e. a) with b) or b) with c). Alternatively, all of steps a), b) and c) may be combined together.

Suitable parameters and amounts of the alcohols selected from the group consisting of $R^1OH$, $R^2OH$, $R^1OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of different identically or differently halogen-substituted phosphines as the phosphorus trihalide. Particular preference is given to $PCl_3$. Further details on the reaction conditions in the preparation of the phosphites I b and for the workup can be taken from DE-A 199 53 058.

The phosphites I b may also be used in the form of a mixture of different phosphites I b as a ligand. Such a mixture may be obtained, for example, in the preparation of the phosphites I b.

However, preference is given to the phosphorus ligand being multidentate, in particular bidentate. The ligand used therefore preferably has the formula II

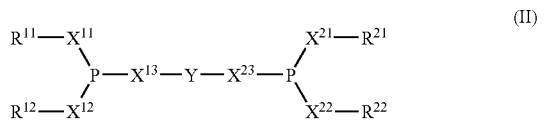

where
$X^{11}, X^{12}, X^{13}, X^{21}, X^{22}, X^{23}$ are each independently oxygen or a single bond
$R^{11}, R^{12}$ are each independently identical or different, separate or bridged organic radicals
$R^{21}, R^{22}$ are each independently identical or different, separate or bridged organic radicals,
Y is a bridging group.

In the context of the present invention, compound II is a single compound or a mixture of different compounds of the aforementioned formula.

In a preferred embodiment, $X^{11}, X^{12}, X^{13}, X^{21}, X^{22}, X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphinite or phosphine, preferably a phosphinite.

In another preferred embodiment, $X^{11}, X^{12}$ and $X^{13}$ may each be a single bond, so that the phosphorus atom surrounded by $X^{11}, X^{12}$ and $X^{13}$ is the central atom of a phosphine. In such a case, $X^{21}, X^{22}$ and $X^{23}$ may each be oxygen, or $X^{21}, X^{22}$ and $X^{23}$ may each be a single bond, so that the phosphorus atom surrounded by $X^{21}, X^{22}$ and $X^{23}$ may be the central atom of a phosphite or phosphine, preferably a phosphine. The bridging group Y is preferably an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be identical or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals may also each be separate or bridged. The $R^{11}, R^{12}, R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, 20 and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application of reference number DE 103 50 999.2 of Oct. 30, 2003, which had not been published at the priority date of the present application.

The compounds I, I a, I b and II described and their preparation are known per se. The phosphorus ligands used may also be mixtures comprising at least two of the compounds I, I a, I b and II.

In a particularly preferred embodiment of the process according to the invention, the phosphorus ligand of the nickel(0) complex and/or the free phosphorus ligand is selected from tritolyl phosphite, bidentate phosphorus chelate ligands and the phosphites of the formula I b

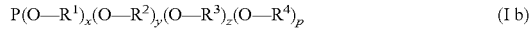    (I b)

where $R^1$, $R^2$ and $R^3$ are each independently selected from o-isopropylphenyl, m-tolyl and p-tolyl, $R^4$ is phenyl; x is 1 or 2, and y, z, p are each independently 0, 1 or 2 with the proviso that x+y+z+p=3; and mixtures thereof.

Lewis Acid or Promoter

In the context of the present invention, a Lewis acid is either a single Lewis acid or else a mixture of a plurality of, for example two, three or four, Lewis acids.

Useful Lewis acids are inorganic or organic metal compounds in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(O\text{-isopropyl})_3$, $MnCl_2$, $ScCl_3$, $AlCl_3$, $(C_8H_{17})AlCl_2$, $(C_8H_{17})_2AlCl$, $(i\text{-}C_4H_9)_2AlCl$, $(C_6H_5)_2AlCl$, $(C_6H_5)AlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$, as described, for example, in U.S. Pat. No. 6,127,567, U.S. Pat. No. 6,171,996 and U.S. Pat. No. 6,380,421. Also useful are metal salts such as $ZnCl_2$, $CoI_2$ and $SnCl_2$, and organometallic compounds such as $RAlCl_2$, $R_2AlCl$, $RSnO_3SCF_3$ and $R_3B$, where R is an alkyl or aryl group, as described, for example, in U.S. Pat. No. 3,496,217, U.S. Pat. No. 3,496,218 and U.S. Pat. No. 4,774,353.

According to U.S. Pat. No. 3,773,809, the promoter used may also be a metal in cationic form which is selected from the group consisting of zinc, cadmium, beryllium, aluminum, gallium, indium, thallium, titanium, zirconium, hafnium, erbium, germanium, tin, vanadium, niobium, scandium, chromium, molybdenum, tungsten, manganese, rhenium, palladium, thorium, iron and cobalt, preferably zinc, cadmium, titanium, tin, chromium, iron and cobalt, and the anionic moiety of the compound may be selected from the group consisting of halides such as fluoride, chloride, bromide and iodide, anions of lower fatty acids having from 2 to 7 carbon atoms, $HPO_3^{2-}$, $H_3PO^{2-}$, $CF_3COO^-$, $C_7H_{15}OSO_2^-$ or $SO_4^{2-}$. Further suitable promoters disclosed by U.S. Pat. No. 3,773,809 are borohydrides, organoborohydrides and boric esters of the formula $R_3B$ and $B(OR)_3$, where R is selected from the group consisting of hydrogen, aryl radicals having from 6 to 18 carbon atoms, aryl radicals substituted by alkyl groups having from 1 to 7 carbon atoms and aryl radicals substituted by cyano-substituted alkyl groups having from 1 to 7 carbon atoms, advantageously triphenylboron.

Moreover, as described in U.S. Pat. No. 4,874,884, it is possible to use synergistically active combinations of Lewis acids, in order to increase the activity of the catalyst system. Suitable promoters may, for example, be selected from the group consisting of $CdCl_2$, $FeCl_2$, $ZnCl_2$, $B(C_6H_5)_3$ and $(C_6H_5)_3SnX$ where $X=CF_3SO_3$, $CH_3C_6H_4SO_3$ or $(C_6H_5)_3BCN$, and the preferred ratio specified of promoter to nickel is from about 1:16 to about 50:1.

In the context of the present invention, the term Lewis acid also includes the promoters specified in U.S. Pat. No. 3,496,217, U.S. Pat. No. 3,496,218, U.S. Pat. No. 4,774,353, U.S. Pat. No. 4,874,884, U.S. Pat. No. 6,127,567, U.S. Pat. No. 6,171,996 and U.S. Pat. No. 6,380,421.

Particularly preferred Lewis acids among those mentioned are in particular metal salts, more preferably metal halides, such as fluorides, chlorides, bromides, iodides, in particular chlorides, of which particular preference is in turn given to zinc chloride, iron(II) chloride and iron(III) chloride.

The process according to the invention distinctly reduces or entirely prevents the undesired rag formation. The extraction apparatus is not flooded with rag and can be operated without disruption even over a prolonged period. The recovery of the catalyst in the hydrocarbon phase (stream II) is just as good as in the prior art processes.

The optional treatment with ammonia or amines, the optional removal of the solid and the optional delay zone allows the process to be further optimized, the rag formation to be further reduced and the separating performance of the extraction to be adjusted.

EXAMPLES

The nonpolar aprotic liquid L and the hydrocarbon H (extractant) used were n-heptane.

The reaction effluent of the hydrocyanation of pentenenitrile to adiponitrile which was used had the following composition:
- 29.5% by weight of $C_6$ dinitriles: inter alia, adiponitrile, 2-methylglutaronitrile, ethylsuccinonitrile,
- 51.3% by weight of $C_5$ mononitriles: predominantly trans-3-pentenenitrile, and also further linear pentenenitrile isomers, and
- 19.2% by weight of catalyst components: inter alia, Ni(0)-tritolyl phosphite complexes, free tritolyl phosphite ligands, zinc chloride and degradation products of the catalyst and of tritolyl phosphite.

Noninventive Example A

No Addition of Heptane Before the Extraction

The reaction effluent, obtained at a mass flow rate of 78 kg/h, was concentrated to an extent of 38 kg/h to 40 kg/h by distillation at an absolute pressure of 5 mbar in a vessel with pumped circulation. A concentrated effluent of the following composition was obtained:
- 57.5% by weight of $C_6$ dinitriles,
- 5% by weight of $C_5$ mononitriles, and
- 37.5% by weight of catalyst components.

This concentrated effluent was extracted with 120 kg/h of n-heptane in countercurrent in a countercurrent extraction column having a sheet metal packing comprising 7 theoretical plates and an internal diameter of 100 mm. The dispersion direction was selected in such a way that n-heptane was the continuous phase. The column was heated by jacket heating with warm water of inlet temperature 70° C.

The column exhibited considerable rag formation and it was completely filled with rag after approx. 17 h of operating time. The extraction had to be terminated because it could no longer be operated in this way.

Inventive Example 1

Addition of Heptane Before the Extraction

The reaction effluent was concentrated as described in example A. The concentrated effluent (see example A for composition) was mixed with 20 kg/h of n-heptane in a pumped circuit. The pumped circuit consisted of approx. 10 m of pipeline having an internal diameter of 15 mm and a gearpump as the circulation pump which worked against an overflow valve which opened at 5 bar gauge. The pump conveyed a volume flow rate of 500 l/h.

After leaving the pumped circuit, the stream I obtained was passed into a 50 l glass vessel (as a delay zone). From an overflow of the glass vessel, a stream I exited and was fed to the lower end of an extraction column. The extraction column and its operating conditions were identical to example A, with the exception that 100 kg/h of n-heptane were fed at the top of the column.

Even after an operating time of 11 days, the column did not show any rag formation and could be operated without disruption. A heptane phase (stream II) and a nitrile phase (stream III) were drawn off.

In order to assess the efficiency of the extraction, the heptane phase and the nitrile phase were analyzed for Ni(0) by means of cyclic voltametry and for phosphorus by means of atomic absorption spectroscopy. The heptane phase contained 99.4% of the Ni(0) and 99.2% of the phosphorus from the feed of the extraction; in the nitrile phase, no Ni(0) and 0.7% of the phosphorus could be detected.

The examples show that the undesired rag formation was completely absent in the process according to the invention. At the same time, the efficiency of the extraction was not impaired.

What is claimed is:

1. A process for extractively removing homogeneously dissolved catalysts from a reaction effluent of a hydrocyanation of unsaturated mononitriles to dinitriles reaction with a hydrocarbon H, comprising
    a) concentrating the reaction effluent before step b) by distillation at pressures of from 0.1 to 5000 mbar and temperatures of from 10 to 150° C.,
    b) adding a hydrocarbon H to the concentrated reaction effluent to obtain a stream I, and
    c) feeding stream I, without prior separation of liquid phases, into an extraction apparatus and extracting it at a temperature T with the hydrocarbon H to obtain a stream II comprising the hydrocarbon H enriched with the catalyst and a stream III having a low catalyst content,
    further comprising treating the reaction effluent with ammonia or a primary, secondary or tertiary, aromatic or aliphatic amine before step b), or treating stream I with ammonia or the primary, secondary or tertiary, aromatic or aliphatic amine.

2. The process according to claim 1, further comprising adding ammonia or a primary, secondary or tertiary, aromatic or aliphatic amine together with the hydrocarbon H.

3. The process according to claim 2, further comprising removing solids precipitating in step b) from stream I before step c).

4. The process according to claim 1, further comprising removing solids precipitating in step b) from stream I before step c).

5. The process according to claim 4, wherein the removing the solids is carried out before, during or after the treatment with ammonia or a primary, secondary or tertiary, aromatic or aliphatic amine of the reaction effluent.

6. The process according to claim 1, wherein the catalyst is a nickel(0) complex having phosphorus ligands and/or free phosphorus ligands.

7. The process according to claim 1, wherein the mononitrile is 3-pentenenitrile and the dinitrile is adiponitrile.

8. The process according to claim 1, further comprising obtaining the reaction effluent by reacting 3-pentenenitrile with hydrogen cyanide in the presence of at least one nickel (0) complex having phosphorus ligands, and optionally in the presence of at least one Lewis acid.

9. The process according to claim 1, wherein the hydrocarbon H used is cyclohexane, methylcyclohexane, n-heptane or n-octane.

10. The process according to claim 1, further comprising mixing a nonpolar aprotic liquid L with the reaction effluent in step a) in a stirred vessel or a pumped circulation system.

11. The process according to claim 10, wherein the nonpolar aprotic liquid L is part of stream II.

12. The process according to claim 10, further comprising adjusting at least one of the three streams, reaction effluent, nonpolar aprotic liquid L and stream I, to a temperature T* which is at least 5° C. below the temperature T.

13. The process according to claim 1, further comprising carrying out the extraction in step c) in a countercurrent extraction column which is equipped with sheet metal packings as dispersing elements.

14. The process according to claim 1, further comprising carrying out the extraction in step c) in countercurrent in a compartmented, stirred extraction column.

15. The process according to claim 1, further comprising conducting stream I through a delay zone after step a) and before step b).

16. The process according to claim 15, wherein the average residence time of stream I in the delay zone is at least 1 min.

17. The process according to claim 1, wherein a flow rate of stream I in all pipelines used in the process is at least 2 m/s.

* * * * *